US011104897B2

(12) United States Patent
Buj Bello et al.

(10) Patent No.: US 11,104,897 B2
(45) Date of Patent: Aug. 31, 2021

(54) COMPOSITIONS AND METHODS FOR THE TREATMENT OF NUCLEOTIDE REPEAT EXPANSION DISORDERS

(71) Applicants: GENETHON, Evry (FR); INSERM (INSTITUT NATIONAL DE LA SANTE ET DE LA RECHERCHE MEDICALE), Paris (FR); UNIVERSITE D'EVRY VAL D'ESSONNE, Evry (FR)

(72) Inventors: Ana Maria Buj Bello, Paris (FR); Mirella Lo Scrudato, Paris (FR)

(73) Assignees: GENETHON, Evry (FR); INSERM (INSTITUT NATIONAL DE LA SANTE ET DE LA RECHERCHE MEDICALE), Paris (FR); UNIVERSITE D'EVRY VAL D'ESSONNE, Evry (FR)

( * ) Notice: Subject to any disclaimer, the term of this patent is extended or adjusted under 35 U.S.C. 154(b) by 629 days.

(21) Appl. No.: 15/569,203

(22) PCT Filed: Apr. 27, 2016

(86) PCT No.: PCT/EP2016/059346
§ 371 (c)(1),
(2) Date: Oct. 25, 2017

(87) PCT Pub. No.: WO2016/174056
PCT Pub. Date: Nov. 3, 2016

(65) Prior Publication Data
US 2018/0100144 A1 Apr. 12, 2018

Related U.S. Application Data

(60) Provisional application No. 62/153,633, filed on Apr. 28, 2015.

(30) Foreign Application Priority Data

Apr. 27, 2015 (EP) .................................... 15305646

(51) Int. Cl.
| C12N 15/113 | (2010.01) |
| A61K 48/00 | (2006.01) |
| C12N 15/11 | (2006.01) |
| C12N 5/10 | (2006.01) |
| C12N 15/10 | (2006.01) |

(52) U.S. Cl.
CPC .......... *C12N 15/102* (2013.01); *C12N 15/111* (2013.01); *C12N 2310/10* (2013.01); *C12N 2310/20* (2017.05); *C12N 2320/30* (2013.01); *C12Q 2521/319* (2013.01)

(58) Field of Classification Search
None
See application file for complete search history.

(56) References Cited

U.S. PATENT DOCUMENTS

| 9,163,284 B2 * | 10/2015 | Liu ....................... C12Q 1/6874 |
| 2010/0055793 A1 * | 3/2010 | Chandrasegaran .. A61K 48/005 435/441 |
| 2017/0088819 A1 * | 3/2017 | Vandendriessche ........................ C12N 5/0658 |

OTHER PUBLICATIONS

Richard, G-F, Shortening trinucleotide repeats using highly specific endonucleases: a possible approach to gene therapy? Opinion| vol. 31, Issue 4, p. 177-186, Apr. 1, 2015.*
Rodriguez et al.: "AAV-CRISPR: a new therapeutic approach to nucleotide repeat diseases", Molecular Therapy, vol. 22, No. Suppl. 1, May 2014 (May 2014), p. S94.
Lo Scrudato et al.: "CRISPR/Cas9-mediated gene editing for type 1 myotonic dystrophy", Human Gene Therapy, vol. 25, No. 11, Nov. 2014 (Nov. 2014), p. A67.
Guy-Franck Richard: "Shortening trinucleotide repeats using highly specific endonucleases: a possible approach to gene therapy?", Trends in Genetics, vol. 31, No. 4, Apr. 1, 2015 (Apr. 1, 2015), pp. 177-186.
Jiang et al.: "RNA-guided editing of bacterial genomes using CRISPR-Cas systems (including Online Methods)", Nature Biotechnology, vol. 31, No. 3, Mar. 2013 (Mar. 2013), pp. 233-239+2PP.
Ran et al.: "Genome engineering using the CRISPR-Cas9 system", Nature Protocols, vol. 8, No. 11, 2013, pp. 2281-2308.

* cited by examiner

*Primary Examiner* — Maria Marvich
(74) *Attorney, Agent, or Firm* — Arrigo, Lee, Guttman & Mouta-Bellum LLP

(57) ABSTRACT

The present invention relates to compositions and methods for the treatment of nucleotide repeat expansion disorders such as myotonic dystrophy.

Figure 2:
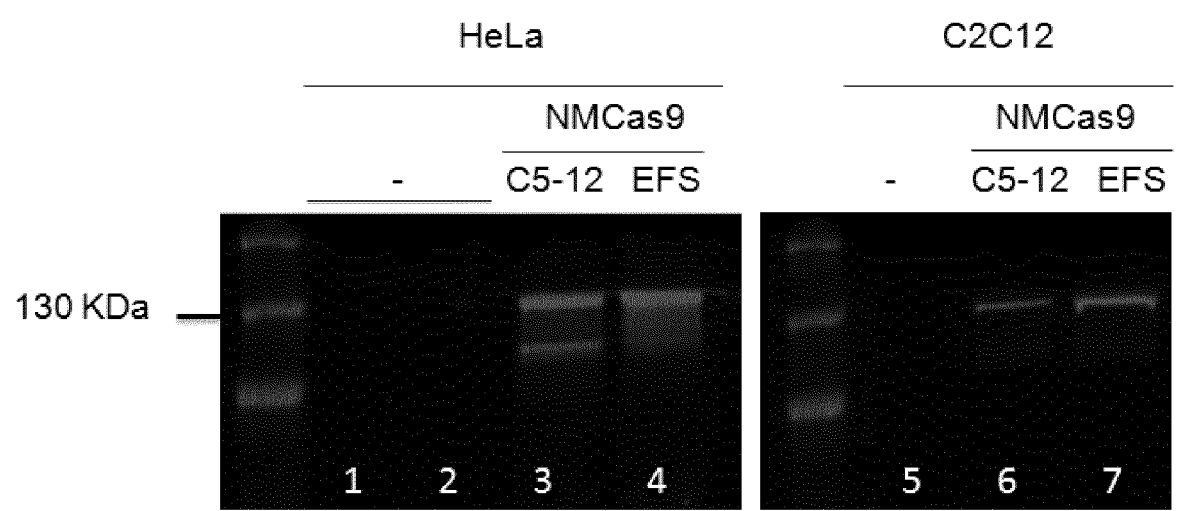

16 Claims, 6 Drawing Sheets
Specification includes a Sequence Listing.

A. C512-NMCas9
B. EFS-NMCas9
C. Double-U6sgRNAs-NM
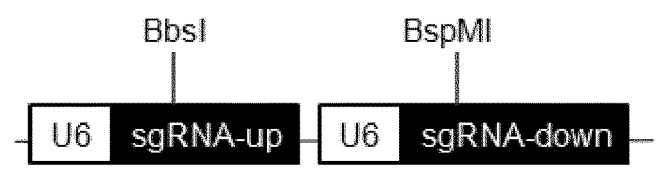
D. DesGFP-Double-U6sgRNAs
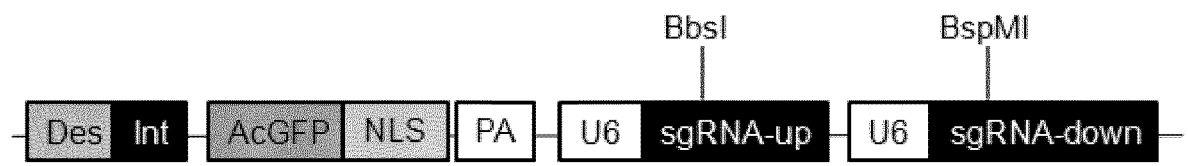
Figure 1

Genome region* surrounding the CTG repeat of the *DMPK* 3'UTR and location of the sgRNAs and protospacer adjacent motifs (PAMs)

*Human genome reference:
Feb.2009 (GRCh37/hg19)
chr19, minus strand
position: 46,272,967(start) - 46,273,898(end)

| LEGEND | |
|---|---|
| NNNNGATT (*AATCNNNN* in the minus strand) | consensus PAM for *Neisseria meningitidis* (NM) CRISPR/Cas9 system[1] |
| NNNNGANT and NNNNGNTT | alternative PAMs[2] |
| TGA | stop codon *DMPK* gene |
| AATAAAA | polyA *DMPK* gene |

[1]Zhang Y et al, Mol Cell 2013
[2]Esvelt KM et al, Nat Methods 2013

```
                                                            F1-DMPK-3'UTR
GTCCCTAGGCCTGGCCTATCGGAGGCGCTTTCCCTGCTCCTGTTCGCCGTTGTTCTGTCTCGTGCCGCCG

CCCTGGGCTGCATTGGGTTGGTGGCCCACGCCGGCCAACTCACCGCAGTCTGGCGCCGCCCAGGAGCCGC
              1                NNNNGANT
CCGCGCTCCCTGAACCCTAGAACTGTCTTCGACTCCGGGGCCCCGTTGGAAGACTGAGTGCCCGGGGCAC

GGCACAGAAGCCGCGCCCACCGCCTGCCAGTTCACAACCGCTCCGAGCGTGGGTCTCCGCCCAGCTCCAG

TCCTGTGATCCGGGCCCGCCCCCTAGCGGCCGGGGAGGGAGGGGCCGGGTCCGCGGCCGGCGAACGGGGC
        7              NNNNGANT
TCGAAGGGTCCTTGTAGCCGGGAATGCTGCTGCTGCTGCTGCTGCTGCTGCTGCTGCTGCTGCTGCTGCT

GCTGCTGCTGCTGCTGGGGGGATCACAGACCATTTCTTTCTTTCGGCCAGGCTGAGGCCCTGACGTGGAT

GGGCAAACTGCAGGCCTGGGAAGGCAGCAAGCCGGGCCGTCCGTGTTCCATCCTCCACGCACCCCCACCT
                                                                   E
ATCGTTGGTTCGCAAAGTGCAAAGCTTTCTTGTGCATGACGCCCTGCTCTGGGGAGCGTCTGGCGCGATC
    NNNNGANT
TCTGCCTGCTTACTCGGGAAATTTGCTTTTGCCAAACCCGCTTTTTCGGGGATCCCGCGCCCCCTCCTC

ACTTGCGCTGCTCTCGGAGCCCCAGCCGGCTCCGCCCGCTTCGGCGGTTTGGATATTTATTGACCTCGTC
                                                AATCNNNN           N
CTCCGACTCGCTGACAGGCTACAGGACCCCCAACAACCCCAATCCACGTTTTGGATGCACTGAGACCCCG

ACATTCCTCGGTATTTATTGTCTGTCCCCACCTAGGACCCCCACCCCGACCCTCGCGAATAAAAGGCCC

TCCATCTGCCCAAAGCTCTGGA
   R1-DMPK-3'UTR
```

Figure 3

SEQUENCE LISTING

```
<160> NUMBER OF SEQ ID NOS: 19

<210> SEQ ID NO 1
<211> LENGTH: 24
<212> TYPE: RNA
<213> ORGANISM: artificial
<220> FEATURE:
<223> OTHER INFORMATION: sgRNA 1 guide sequence

<400> SEQUENCE: 1
gcgcucccug aacccuagaa cugu                                              24

<210> SEQ ID NO 2
<211> LENGTH: 24
<212> TYPE: RNA
<213> ORGANISM: artificial
<220> FEATURE:
<223> OTHER INFORMATION: sgRNA 7 guide sequence

<400> SEQUENCE: 2
acggggcucg aagggccuu guag                                               24

<210> SEQ ID NO 3
<211> LENGTH: 24
<212> TYPE: RNA
<213> ORGANISM: artificial
<220> FEATURE:
<223> OTHER INFORMATION: sgRNA E guide sequence

<400> SEQUENCE: 3
uggggagcgu cuggcgcgau cucu                                              24

<210> SEQ ID NO 4
<211> LENGTH: 24
<212> TYPE: RNA
<213> ORGANISM: artificial
<220> FEATURE:
<223> OTHER INFORMATION: sgRNA N guide sequence

<400> SEQUENCE: 4 gucgggucu cagugcaucc aaaa                                               24
```

<210> SEQ ID NO 5
<211> LENGTH: 137
<212> TYPE: RNA
<213> ORGANISM: artificial
<220> FEATURE:
<223> OTHER INFORMATION: sgRNA 1

<400> SEQUENCE: 5
gcgcucccug aacccuagaa cuguguugua gcucccuuuc gaaagaaccg uugcuacaau      60
aaggccgucu gaaaagaugu gccgcaacgc ucugccccuu aaagcuucug cuuuaagggg     120
caucguuuau uuuuuuu                                                    137

<210> SEQ ID NO 6
<211> LENGTH: 138
<212> TYPE: RNA
<213> ORGANISM: artificial
<220> FEATURE:
<223> OTHER INFORMATION: sgRNA 7

<400> SEQUENCE: 6
gacggggcuc gaaggguccu uguagguugu agcucccuuu cgaaagaacc guugcuacaa      60
uaaggccguc ugaaaagaug ugccgcaacg cucugccccu aaagcuucu gcuuuaaggg      120 gcaucguuua uuuuuuuu                                                   138

<210> SEQ ID NO 7
<211> LENGTH: 138
<212> TYPE: RNA
<213> ORGANISM: artificial
<220> FEATURE:
<223> OTHER INFORMATION: sgRNA E

<400> SEQUENCE: 7
guggggagcg ucggcgcga ucucuguugu agcucccuuu cgaaagaacc guugcuacaa      60
uaaggccguc ugaaaagaug ugccgcaacg cucugccccu aaagcuucu gcuuuaaggg      120 gcaucguuua uuuuuuuu                                                   138

<210> SEQ ID NO 8
<211> LENGTH: 137
<212> TYPE: RNA
<213> ORGANISM: artificial
<220> FEATURE:
<223> OTHER INFORMATION: sgRNA N

<400> SEQUENCE: 8 gucgggucu cagugcaucc aaaaguugua gcucccuuuc gaaagaaccg uugcuacaau      60
aaggccgucu gaaaagaugu gccgcaacgc ucugccccuu aaagcuucug cuuuaagggg     120
caucguuuau uuuuuuu                                                    137

<210> SEQ ID NO 9
<211> LENGTH: 263
<212> TYPE: DNA
<213> ORGANISM: artificial
<220> FEATURE:
<223> OTHER INFORMATION: U6 promoter

<400> SEQUENCE: 9
aggtcgggca ggaagagggc ctatttccca tgattccttc atatttgcat atacgataca      60
aggctgttag agagataatt agaattaatt tgactgtaaa cacaaagata ttagtacaaa     120
atacgtgacg tagaaagtaa taatttcttg ggtagtttgc agttttaaaa ttatgtttta    180
aaatggacta tcatatgctt accgtaactt gaaagtattt cgatttcttg gctttatata        240
tcttgtggaa aggacgaaac acc                                              263

<210> SEQ ID NO 10
<211> LENGTH: 402
<212> TYPE: DNA
<213> ORGANISM: artificial
<220> FEATURE:
<223> OTHER INFORMATION: sgRNA 1 cassette

<400> SEQUENCE: 10
aggtcgggca ggaagagggc ctatttccca tgattccttc atatttgcat atacgataca         60
aggctgttag agagataatt agaattaatt tgactgtaaa cacaaagata ttagtacaaa        120
atacgtgacg tagaaagtaa taatttcttg ggtagtttgc agttttaaaa ttatgtttta        180
aaatggacta tcatatgctt accgtaactt gaaagtattt cgatttcttg gctttatata        240
tcttgtggaa aggacgaaac accgcgctcc ctgaaccctn gaactgtgtt gtagctccct        300
ttcgaaagaa ccgttgctac aataaggccg tctgaaaaga tgtgccgcaa cgctctgccc        360
cttaaagctt ctgctttaag gggcatcgtt tatttttttt aa                          402

<210> SEQ ID NO 11
<211> LENGTH: 403
<212> TYPE: DNA
<213> ORGANISM: artificial
<220> FEATURE:
<223> OTHER INFORMATION: sgRNA 7 cassette

<400> SEQUENCE: 11
aggtcgggca ggaagagggc ctatttccca tgattccttc atatttgcat atacgataca         60
aggctgttag agagataatt agaattaatt tgactgtaaa cacaaagata ttagtacaaa        120
atacgtgacg tagaaagtaa taatttcttg ggtagtttgc agttttaaaa ttatgtttta        180
aaatggacta tcatatgctt accgtaactt gaaagtattt cgatttcttg gctttatata        240
tcttgtggaa aggacgaaac accgacgggg ctcgaagggt ccttgtaggt tgtagctccc        300
tttcgaaaga accgttgcta caataaggcc gtctgaaaag atgtgccgca acgctctgcc        360
ccttaaagct tctgctttaa ggggcatcgt ttatttttttt taa                        403

<210> SEQ ID NO 12
<211> LENGTH: 403
<212> TYPE: DNA
<213> ORGANISM: artificial
<220> FEATURE:
<223> OTHER INFORMATION: sgRNA E cassette

<400> SEQUENCE: 12
aggtcgggca ggaagagggc ctatttccca tgattccttc atatttgcat atacgataca         60
aggctgttag agagataatt agaattaatt tgactgtaaa cacaaagata ttagtacaaa        120
atacgtgacg tagaaagtaa taatttcttg ggtagtttgc agttttaaaa ttatgtttta        180
aaatggacta tcatatgctt accgtaactt gaaagtattt cgatttcttg gctttatata        240
tcttgtggaa aggacgaaac accgtgggga gcgtctggcg cgatctctgt tgtagctccc        300
tttcgaaaga accgttgcta caataaggcc gtctgaaaag atgtgccgca acgctctgcc        360
ccttaaagct tctgctttaa ggggcatcgt ttatttttttt taa                        403

<210> SEQ ID NO 13

```
<211> LENGTH: 402
<212> TYPE: DNA
<213> ORGANISM: artificial
<220> FEATURE:
<223> OTHER INFORMATION: sgRNA N cassette

<400> SEQUENCE: 13
aggtcgggca ggaagagggc ctatttccca tgattccttc atatttgcat atacgataca      60
aggctgttag agagataatt agaattaatt tgactgtaaa cacaaagata ttagtacaaa     120
atacgtgacg tagaaagtaa taatttcttg ggtagtttgc agttttaaaa ttatgtttta    180
aaatggacta tcatatgctt accgtaactt gaaagtattt cgatttcttg gctttatata    240
tcttgtggaa aggacgaaac accgtcgggg tctcagtgca tccaaaagtt gtagctccct    300
ttcgaaagaa ccgttgctac aataaggccg tctgaaaaga tgtgccgcaa cgctctgccc    360
cttaaagctt ctgctttaag gggcatcgtt tatttttttt aa                       402

<210> SEQ ID NO 14
<211> LENGTH: 932
<212> TYPE: DNA
<213> ORGANISM: homo sapiens

<400> SEQUENCE: 14
gtccctaggc ctggcctatc ggaggcgctt tccctgctcc tgttcgccgt tgttctgtct     60
cgtgccgccg ccctgggctg cattgggttg gtggcccacg ccggccaact caccgcagtc    120
tggcgccgcc caggagccgc ccgcgctccc tgaaccctag aactgtcttc gactccgggg    180
ccccgttgga agactgagtg cccggggcac ggcacagaag ccgcgcccac cgcctgccag    240
ttcacaaccg ctccgagcgt gggtctccgc ccagctccag tcctgtgatc cgggcccgcc    300
ccctagcggc cggggaggga ggggccgggt ccgcggccgg cgaacggggc tcgaagggtc    360
cttgtagccg ggaatgctgc tgctgctgct gctgctgctg ctgctgctgc tgctgctgct    420
gctgctgctg ctgctggggg gatcacagac catttctttc tttcggccag gctgaggccc    480
tgacgtggat gggcaaactg caggcctggg aaggcagcaa gccgggccgt ccgtgttcca    540
tcctccacgc accccacct atcgttggtt cgcaaagtgc aaagctttct tgtgcatgac     600
gccctgctct ggggagcgtc tggcgcgatc tctgcctgct tactcgggaa atttgctttt    660
gccaaacccg cttttcgggg gatcccgcgc cccctcctc acttgcgctg ctctcggagc     720
cccagccggc tccgcccgct tcggcggttt ggatatttat tgacctcgtc ctccgactcg    780
ctgacaggct acaggacccc caacaacccc aatccacgtt ttggatgcac tgagaccccg    840
acattcctcg gtatttattg tctgtcccca cctaggaccc ccaccccga ccctcgcgaa     900
taaaaggccc tccatctgcc caaagctctg ga                                  932

<210> SEQ ID NO 15
<211> LENGTH: 32
<212> TYPE: DNA
<213> ORGANISM: artificial
<220> FEATURE:
<223> OTHER INFORMATION: target name 1

<400> SEQUENCE: 15
gcgctccctg aaccctagaa ctgtcttcga ct                                   32

<210> SEQ ID NO 16
<211> LENGTH: 32
<212> TYPE: DNA
<213> ORGANISM: artificial
```

```
<220> FEATURE:
<223> OTHER INFORMATION: target name 7

<400> SEQUENCE: 16
acggggctcg aagggtcctt gtagccggga at                                    32

<210> SEQ ID NO 17
<211> LENGTH: 32
<212> TYPE: DNA
<213> ORGANISM: artificial
<220> FEATURE:
<223> OTHER INFORMATION: target name E

<400> SEQUENCE: 17
tggggagcgt ctggcgcgat ctctgcctgc tt                                    32

<210> SEQ ID NO 18
<211> LENGTH: 32
<212> TYPE: DNA
<213> ORGANISM: artificial
<220> FEATURE:
<223> OTHER INFORMATION: target name N

<400> SEQUENCE: 18
gtcggggtct cagtgcatcc aaaacgtgga tt                                    32

<210> SEQ ID NO 19
<211> LENGTH: 18
<212> TYPE: DNA
<213> ORGANISM: artificial
<220> FEATURE:
<223> OTHER INFORMATION: #15 right part

<400> SEQUENCE: 19
ccacgacatt cctcggta                                                    18
```

COMPOSITIONS AND METHODS FOR THE TREATMENT OF NUCLEOTIDE REPEAT EXPANSION DISORDERS

SEQUENCE LISTING

The instant application contains a Sequence Listing which has been submitted electronically in ASCII format and is hereby incorporated by reference in its entirety. Said ASCII copy, created on Oct. 2, 2017, is named B2019PC00-SEQ_LIST_ST25.txt and is 6,684 bytes in size.

FIELD OF THE INVENTION

The present invention relates to compositions and methods for the treatment of nucleotide repeat expansion disorders such as myotonic dystrophy.

BACKGROUND OF THE INVENTION

Nucleotide repeat expansions, especially trinucleotide repeat expansions, are involved in more than two dozens neurological and developmental disorders. One approach that has been proposed to treat these diseases is to shorten repeats to non-pathological lengths using highly specific nucleases (see for a review Richard G F, Trends Genet. 2015 April; 31(4):177-186).

Highly specific nucleases such as meganucleases, ZFNs, TALENs and CRISPR-Cas9 nucleases have been used in such strategies. However, the latter was considered by those skilled in the art to be inappropriate for the excision of trinucleotide repeat expansions (see Richard cited supra). Overall, TALENs were considered a more promising tool for shortening trinucleotide repeats.

Against this strong prejudice, the present inventors show that the CRISPR-Cas9 system may be implemented to excise nucleotide repeat expansions from genomic DNA, thereby providing a powerful and unexpected tool for treating nucleotide repeat expansion disorders.

SUMMARY OF THE INVENTION

The inventors have shown that, against the strong prejudice developed above, the CRISPR-Cas9 system may be efficient for the treatment of nucleotide repeat expansion disorders.

In one aspect, disclosed herein are single guide RNA (sgRNA) molecules useful for specifically excising a nucleotide repeat expansion, especially a trinucleotide repeat expansion, from a non-coding region of a gene of interest. The sgRNA molecules disclosed herein are able to bind by base-pairing a sequence complement to a genomic DNA target (protospacer) sequence which is 5' or 3' from the targeted nucleotide expansion, and are able to recruit a Cas9 endonuclease to, or near, the site of hybridization between the sgRNA and genomic DNA. The sgRNA molecules of the invention comprise all the sequence elements appropriate for inducing Cas9-mediated double-strand breaks in the vicinity of the site of complementarity. In particular, the present application discloses sgRNA pairs appropriate for effecting an excision of the nucleotide repeat expansion present in the non-coding region of the gene of interest, wherein the pair of sgRNAs comprises a first sgRNA which is complementary to a genomic DNA sequence 5' from the nucleotide repeat expansion and a second sgRNA which is complementary to a genomic DNA sequence 3' from the nucleotide repeat expansion.

In a particular embodiment, the sgRNA molecule comprises a sequence selected from the group consisting of SEQ ID NO:1 to 4. In another particular embodiment, the sgRNA molecule have the sequence shown in any one of SEQ ID NO:5 to 8.

Another aspect disclosed herein is the use of the CRISPR-Cas9 system for excising a nucleotide repeat expansion. In particular, the nucleotide repeat expansion is within the genomic DNA of a target cell, more particularly within a non-coding region of a gene present in said genomic DNA.

According to a further aspect, herein is disclosed a method for excising a nucleotide repeat expansion from a non-coding region of a gene in the genomic DNA of a cell, said method implementing the CRISPR-Cas9 system. The method may comprise introducing into the cell a pair of sgRNA molecules and a gene coding a Cas9 endonuclease.

In another aspect, disclosed herein is a method for treating a nucleotide repeat expansion disorder, wherein said repeat is excised from a gene of interest, comprising such a nucleotide repeat expansion, using at least a pair of sgRNA molecules as described above and a Cas9 endonuclease.

More specifically, the uses and methods of the invention may comprise introducing into a cell, such as a cell of a subject in need thereof:
(i) a first sgRNA molecule;
(ii) a second sgRNA molecule; and
(iii) a CRISPR/Cas9 endonuclease;
wherein said first and a second sgRNA are complementary to a sequence located at 5' and 3' from said nucleotide repeat expansion, respectively, thereby being appropriate for excising said nucleotide repeat expansion.

In a particular embodiment, the nucleotide repeat expansion is within an intron or a 3'-untranslated region of the gene of interest. In a more particular embodiment, the nucleotide repeat expansion is within the 3'-untranslated region of the gene of interest In a further particular embodiment, the gene of interest is FMR1, AFF2 or FMR2, AFF3, FXN, ATXN80S/ATXN8, ATXN10, PPP2R2B, BEAN1/TK2, NOP56, C9ORF72, ZN9/CNBP or DMPK. In a particular embodiment, the gene of interest is DMPK. In a variant of this embodiment, the nucleotide repeat expansion is in the 3'-untranslated region of the DMPK coding gene.

In some other specific embodiments, the nucleotide repeat expansion disorder is myotonic dystrophy, in particular Myotonic dystrophy type 1 (DM1) or type 2 (DM2), more particularly DM1.

In some embodiments, the sgRNA molecule comprises a guide RNA sequence having from 15 to 40 nucleotides, in particular from 20 to 30 nucleotides, in particular from 22 to 26 nucleotides, such as 22, 23, 24, 25, 26 nucleotides and a scaffold RNA sequence. In a particular embodiment, the sgRNA molecule comprises a guide RNA sequence consisting of 24 nucleotides.

In some embodiments, the sgRNA molecules are designed to bind by base-pairing the complement to the genomic DNA target sequence (otherwise referred to as the target sequence). This target sequence is called the protospacer and is located next to a nucleotide motif called PAM (Protospacer adjacent motif) that is recognized by the implemented Cas9 endonuclease.

In some embodiments, the Cas9 endonuclease and/or the sgRNA molecules are expressed from one or several vectors, such as one or several plasmids or viral vectors. For example, the Cas9 endonuclease may be expressed from a first vector, and the first and second sgRNA molecules may be either expressed from a single, second vector, or one from a second vector and the other one from a third vector. In another embodiment, all the elements necessary for the implementation of the CRISPR-Cas9 system are contained in a single vector.

In a further aspect, it is herein disclosed a kit comprising a Cas9 endonuclease and a first and second sgRNA molecules as described above. In another aspect, it is herein disclosed a kit comprising a vector encoding a Cas9 endonuclease and a vector encoding the first and/or the second sgRNA molecules as described above, or a single vector which expresses the Cas9 endonuclease and one or both sgRNA molecules. As mentioned above, the vector(s) in the kit may be a plasmid vector or a viral vector. In addition, the kit according to the invention may include any further reagent (such as buffer(s) and/or one or more transfection reagent) or devices useful in the implementation of the methods and uses disclosed herein.

Other aspects and embodiments of the invention will be apparent in the following detailed description.

LEGENDS OF THE FIGURES

FIG. 1. Cas9 and sgRNAs expression cassettes. A and B: Cas9 from *Neisseria meningitidis* (NMCas9) was cloned under either a synthetic muscle-specific (C5-12) or a ubiquitous (EFS: shorter EF-1α) promoter. Int: chimeric intron; NLS: nuclear localization signal; HA: human influenza hemagglutinin epitope; 3XFLAG: 3 tandem FLAG epitopes; SVpolyA: simian virus 40 polyadenylation signal. C and D: expression cassette for two sgRNAs, both under the control of the U6 promoter but containing different cloning sites for the sgRNA protospacer, BbsI and BspMI. A nuclear GFP coding sequence (AcGFP) under the Desmin promoter (Des) is also present in construct D.

FIG. 2. Detection of NMCas9 in cells lines. Western blot analysis of NMCas9 (MW: 130.6 KDa) expressed in HeLa (lanes 1 to 4) and C2C12 (lanes 5 to 7) cells transfected with control plasmid ((−); lane 1: pC512-Int-smSV40; lanes 2 and 5: pEFS-Int-SVpolyA)) or with a plasmid harboring the NMCas9 (lanes 3 and 6: pC512-Int-NMCas9-smSVpolyA, see FIG. 1 construct A; lanes 4 and 7: pEFS-Int-NMCas9-SVpolyA, see FIG. 1 construct B). Specific detection of the protein was done by an antibody directed against the 3 tandem FLAG epitopes located at the C-terminus of the protein. HeLa: human epithelial carcinoma cell line; C2C12: mouse myoblast cell line; C5-12: synthetic muscle-specific promoter; EFS: EF-1α shorter ubiquitous promoter.

FIG. 3. Genomic region surrounding the CTG repeats of the DMPK gene (SEQ ID NO:14). Sequence of the genomic DNA targets (protospacers) 1, 7, E and N are underlined, respective PAMs (Protospacer adjacent motifs) are surrounded by a rectangle. CTG repeat is highlighted in black. Positions of the primers used to PCR amplify this region are also underlined. Chromosome: 19; strand: minus; position: 46,272,967(start)-46,273,898(end); Human genome reference: February 2009 (GRCh37/hg19). The polyA signal (nucleotides 899-905 of SEQ ID NO:14) of the DMPK gene is bolded.

Figure 4:
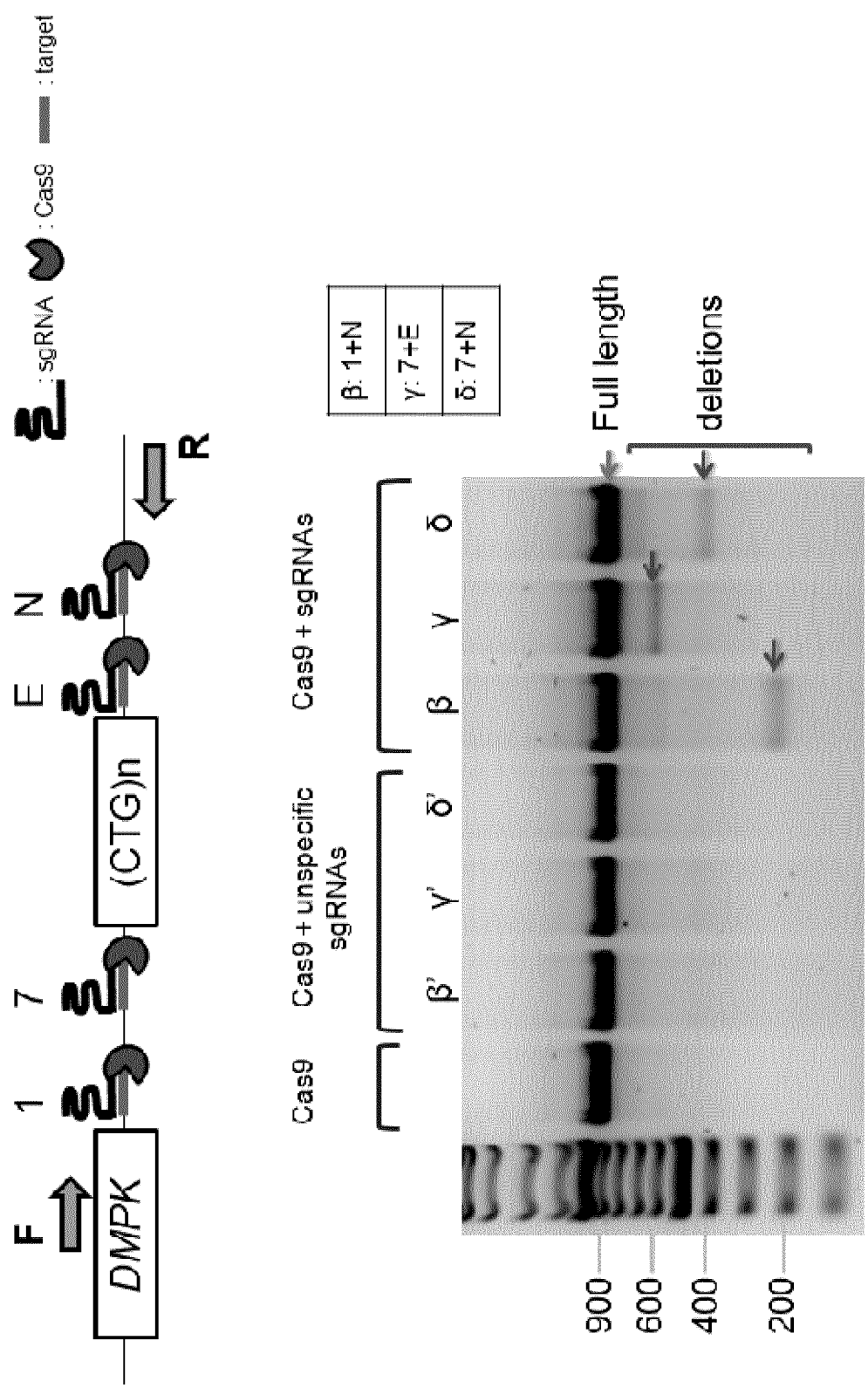

FIG. 4. Detection of the genomic region containing the CTG deletion. DMPK 3'UTR region was PCR amplified from gDNA extracted from HeLa or HEK 293T (not shown) cells with primers F1- and R1-DMPK-3'UTR (shown in FIG. 3). Cells have been transfected only with EFS-NMCas9 (Cas9) or co-transfected with EFS-NMCas9 and the indicated sgRNAs (Cas9+unspecific sgRNAs, β'→δ'; Cas9+ sgRNAs, β→δ), and collected 48 hours later. Full length PCR products and those containing the CTG deletion are indicated with a green and a red arrow, respectively. PCR products' expected sizes are shown in the Table 2. Unspecific sgRNAs target a sequence four nucleotide slided compared to that targeted by the corresponding sgRNA ($N_{24}$ of unspecific sgRNA corresponds to $N_{20}$ of sgRNA).

Figure 5:
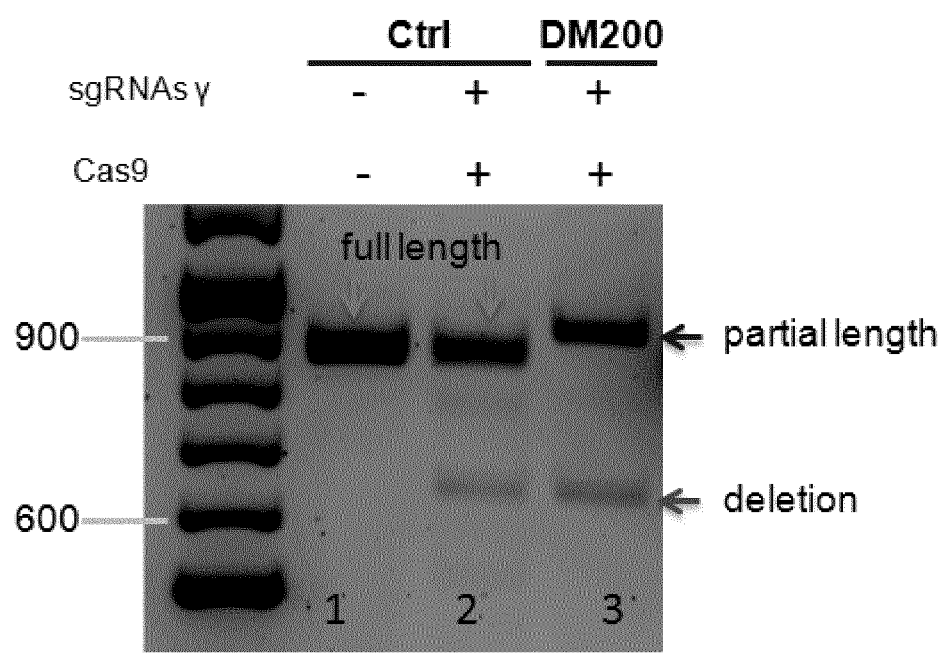

FIG. 5. Deletion of the CTG repeat expansion from DM1 patient primary cells. Fetal primary cells from a control individual (Ctrl) and a DM1 patient harboring 200 CTG repeat (DM200) have been transfected with a GFP control plasmid, lane 1, or co-transfected with sgRNAs γ (construct pAAV-Des-AcGFP-U6sgRNA-NM-7E-DMPK) and EFS-NMCas9 (construct pEFS-Int-NMCas9-SVpolyA), lanes 2 and 3. Cells have been collect two days post transfection and gDNA was extracted from GFP positive sorted cells. DMPK 3' UTR region was PCR amplified as in FIG. 4. Full and partial length PCR products and PCR products containing the CTG deletions are indicated with a green, a blue and a red arrow respectively. PCR products' expected sizes are shown in the Table 2.

Figure 6:
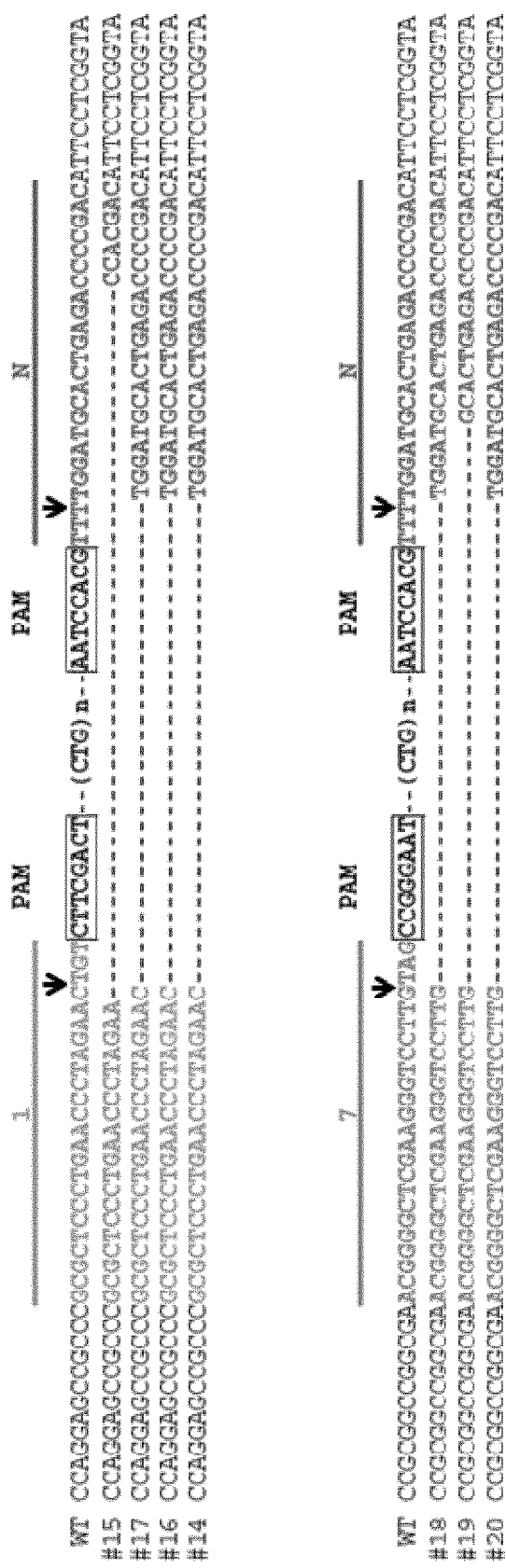

FIG. 6. Sequencing of the genomic region containing the CTG deletion. gDNA extracted from HEK 293T cells transfected with EFS-NMCas9 (construct pEFS-Int-NMCas9-SVpolyA) and the indicated sgRNA couples (β:1 and N; δ:7 and N) was PCR amplified and subcloned into a plasmid. Single clones were sequenced by standard sequencing (Beckman Coulter Genomics) and their sequences were aligned with the wild type original sequence to show the cutting positions. Most of the clones presented a cut between the 3rd and the 4th nucleotide of the targets adjacent to the PAM sequence (indicated by the black arrows).

WT: nucleotides 130-853 of SEQ ID NO:14
15: nucleotides 130-162 of SEQ ID NO:14+SEQ ID NO: 19
17: nucleotides 130-163 of SEQ ID NO:14+nucleotides 822-853 of SEQ ID NO:14
16: nucleotides 130-163 of SEQ ID NO:14+nucleotides 822-853 of SEQ ID NO:14
14: nucleotides 130-163 of SEQ ID NO:14+nucleotides 822-853 of SEQ ID NO:14
WT: nucleotides 331-853 of SEQ ID NO:14
18: nucleotides 331-364 of SEQ ID NO:14+nucleotides 822-853 of SEQ ID NO:14
19: nucleotides 331-364 of SEQ ID NO:14+nucleotides 827-853 of SEQ ID NO:14
20: nucleotides 331-364 of SEQ ID NO:14+nucleotides 822-853 of SEQ ID NO:14

DETAILED DESCRIPTION OF THE INVENTION

The inventors herein show that the CRISPR-Cas9 system may be efficiently used to excise nucleotide repeats from genomic DNA, thereby providing a powerful tool for the treatment of nucleotide repeat expansion disorders such as myotonic dystrophy.

Accordingly, in a first aspect it is herein disclosed
(i) a sgRNA molecule which is able to bind by base-pairing the sequence complement to a target sequence (protospacer) in genomic DNA which is located 5' from a nucleotide repeat located within a non-coding region of a gene of interest,
(ii) a sgRNA molecule which is able to bind by base-pairing the sequence complement to a target sequence (protospacer) in the genomic DNA which is located 3' from a nucleotide repeat located within a non-coding region of a gene of interest, and
(iii) a pair of sgRNA molecules that are each able to bind by base-pairing sequences complement to the target sequences in the genomic DNA which are located 5' and 3', respectively, from a nucleotide repeat located within a non-coding region of a gene of interest.

CRISPR-Cas9 System

The Clustered Regularly Interspaced Short Palindromic Repeats (CRISPR) Type II system is a RNA-guided endonuclease technology that has recently emerged as a promising genome editing tool. There are two distinct components to this system: (1) a guide RNA and (2) an endonuclease, in this case the CRISPR associated (Cas) nuclease, Cas9. The guide RNA is a combination of bacterial CRISPR RNA (crRNA) and a trans-activating crRNA (tracrRNA) engineered into a single chimeric guide RNA (sgRNA) transcript (Jinek et al., Science 2012 Aug. 7; 337(6096):816-21). The sgRNA combines the targeting specificity of the crRNA with the scaffolding properties of the tracrRNA into a single transcript. When the sgRNA and the Cas9 are expressed in the cell, the genomic target sequence can be modified or permanently disrupted.

The sgRNA/Cas9 complex is recruited to the target sequence by the base-pairing between the sgRNA guide sequence and the complement to the target sequence in the genomic DNA (protospacer). For successful binding of Cas9, the genomic target sequence must also contain the correct Protospacer Adjacent Motif (PAM) sequence immediately following the target sequence. The binding of the sgRNA/Cas9 complex localizes the Cas9 to the genomic target sequence so that the Cas9 endonuclease can cut both strands of DNA causing a Double Strand Break (DSB). Cas9 will cut 3-4 nucleotides upstream of the PAM sequence. According to the system implemented in the present invention, the DSB can then be repaired through the Non-Homologous End Joining (NHEJ) repair pathway.

The present invention implements this powerful system in an innovative way, for excising repeat sequences that have been reported to be associated with a number of diseases or disorders.

Cas9 Endonuclease

The DNA-targeting mechanisms of the type II CRISPR-Cas system involves a guide RNA which directs the Cas9 endonuclease to cleave the targeted DNA in a sequence-specific manner, dependent on the presence of a Protospacer Adjacent Motif (PAM) on the targeted DNA.

The PAM sequence varies depending on the species of the bacteria from which the Cas9 endonuclease was derived. Consensus PAM sequences include both primary and secondary PAMs, which may be considered to identify sequences of interests within the target gene of interest. The table below provides a list of PAM sequences for some Cas9 endonucleases derived from different species.

| Species | PAM sequences |
|---|---|
| S. Pyogenes | NGG, NAG |
| S. thermophilus | NNRGAA, NNAGGA, NNANAA, NNGGGA, NGGNG, NNAAAAW |
| N. meningitidis | NNNNGATT, NNNNGNTT, NNNNGANT, NNNNGTTN, NNNNGANN, NNNNGNNT, NNNNGTNN, NNNNGNTN |
| S. mutans | NGG |
| C. jejuni | NNNNACA |
| P. multocida | GNNNCNNA |
| F. novicida | NG |

In a particular embodiment of the invention, the Cas9 endonuclease used in the invention is derived from S. pyogenes, S. thermophilus, N. meningitidis, S. mutans, C. jejuni, F. novicida, S. aureus, P. multocida, P. bettyae, H. parainfluenzae, H. pittmaniae or L. crispatus. In a specific embodiment, wherein the nucleotide repeat expansion to excise is present in the 3'-untranslated region of the DMPK gene, the Cas9 endonuclease is derived from N. meningitidis, S. aureus, S. thermophilus or C. jejuni (Zhang et al., Mol Cell 2013 May 23; 50(4):488-503; Hou et al., 2013 Sep. 24; 110(39):15644-9).

guide-RNAs

It is herein disclosed single guide RNAs (or sgRNAs) that are specifically designed for the excision of a trinucleotide repeat expansion.

As mentioned above, the sgRNA is the part of the CRISPR-Cas9 system that provides genomic DNA targeting specificity to the system. The targeted genomic DNA sequence comprises from 15 to 40 nucleotides, in particular from 20 to 30 nucleotides, in particular from 22 to 26 nucleotides, such as 22, 23, 24, 25, 26 nucleotides, depending on the specific Cas9 endonuclease used in the system, followed by an appropriate Protospacer Adjacent Motif (PAM) as described above. In a particular embodiment, the sgRNA molecule comprises a guide RNA sequence which is complementary to the complement sequence of a genomic sequence from 15 to 40 nucleotides, in particular from 20 to 30 nucleotides, in particular from 22 to 26 nucleotides, such as 22, 23, 24, 25, 26 nucleotides, more specifically to 24 nucleotides, preceding a PAM within the targeted non-coding region of the gene of interest. In a particular embodiment, the guide RNA sequence is either identical or at least 80% identical, preferably at least 85%, 90%, 95%, 96%, 97%, 98%, or at least 99% identical to said genomic sequence and is able to hybridize the complement sequence of said genomic sequence from 15 to 40 nucleotides, in particular from 20 to 30 nucleotides, in particular from 22 to 26 nucleotides, such as 22, 23, 24, 25, 26 nucleotides, more specifically to 24 nucleotides, preceding a PAM within the targeted non-coding region of the gene of interest. As is well known by those skilled in the art, the sgRNA does not contain the PAM motif and as a consequence does not bind to the sequence complement to the PAM. The target sequence may be on either strand of the genomic DNA, within a non-coding region of a gene of interest.

In a particular embodiment, the PAM and at least 4 nucleotides upstream the PAM are in the non-coding region of the gene of interest. In a further particular embodiment, the entire target sequence and the PAM are in the non-coding region of the gene of interest.

Bioinformatics tools are available for identifying target genomic DNA sequences comprising the appropriate PAM(s), depending on the origin of the Cas9 endonuclease used in the practice of the invention, and sequence of hybridization, such as those provided by the following web tools: CRISPR Design, E-CRISP, CasFinder, and CRISPOR. A person skilled in the art can also refer to Doench et al., Nat Biotechnol. 2014 December; 32(12): 1262-7 or Prykhozhij et al., PLoS One. 2015 Mar. 5; 10(3):e0119372 and may find further information and resources on the CRISPR-Cas9 system and on identifying target genomic DNA comprising the appropriate PAM(s) on the website cnb csic es. PAM sequences may alternatively be identified by using such a sequence as a query in sequence alignment tools, such as the BLAST or FASTA algorithm, within a gene of interest.

As is well known, a sgRNA is a fusion of a crRNA and a tracrRNA which provides both targeting specificity (that is conferred by the guide sequence base-pairing to the complement sequence of the target genomic DNA sequence) and scaffolding/binding ability for a Cas9 nuclease. In an embodiment, the tracrRNA moiety and the selected Cas9 endonuclease are derived from the same phylogenic subgroup. A phylogenic tree of representative Cas9 orthologs is described in particular in Fonfara et al., Nucleic Acids Res. 2014 February; 42(4):2577-90. As an illustrative embodiment, one can cite components both derived from the II-A, II-B or II-C bacterial type II CRISPR-Cas system. For example, the tracrRNA may be derived from *N. meningitidis, C. Jejuni* or *P. multocida* and the implemented Cas9 endonuclease is derived from *N. meningitidis*. In a specific embodiment, the tracrRNA moiety and the selected Cas9 endonuclease match, in the sense that both are derived from the same specie to function together. For example, the tracrRNA and the Cas9 endonuclease are both derived from *S. pyogenes, S. thermophilus, N. meningitidis, S. mutans, C. jejuni, F. novicida, S. aureus, P. multocida, P. bettyae, H. parainfluenzae, H. pittmaniae* or *L. crispatus* in a particular embodiment of the invention. More particularly, both the tracrRNA moiety and the Cas9 endonuclease are derived from *N. meningitidis*.

Molecular biology kits and tools, such as appropriate plasmids, are available for easily produce a sgRNA of the desired specificity in terms of both the targeted genomic DNA sequence and the Cas9 endonuclease. For example, a number of plasmids and tools are available from Addgene. In a particular embodiment, the sgRNA or the sgRNA pair is expressed from a plasmid under the control of an U6 promoter. In a particular embodiment, both sgRNAs of the sgRNA pair of the invention are expressed from a single expression cassette containing the two sgRNA scaffolds, each one under the control of a promoter, in particular the U6 promoter, in the same vector (for example in the same plasmid or in the same recombinant viral genome such as in an AAV genome). In a particular embodiment, the two sgRNA scaffolds are provided in reverse position or in tandem, in particular in tandem. In another embodiment, the Cas9 endonuclease coding gene is operably linked to a promoter such as an inducible or constitutive promoter, in particular an ubiquitous or tissue-specific promoter, in particular a muscle-specific promoter. Ubiquitous promoters include, for example, the EFS, CMV or CAG promoter. Muscle-specific promoters include, without limitation, the muscle creatine kinase (MCK) promoter, the desmin promoter or the synthetic C5.12 promoter as is well known in the art. In addition, the promoter used for expression of the Cas9 endonuclease may be an inducible promoter such as a tetracycline-, tamoxifen- or ecdysone-inducible promoter.

In a particular embodiment, the first and second sgRNA molecules are each complementary to a region which is 5' and 3' from the nucleotide repeat expansion to be excised, respectively. The sgRNA molecules are thus designed to bind specifically regions upstream and downstream of the nucleotide repeat expansion with the PAM and at least 4 nucleotides upstream the PAM being in the non-coding region of the gene of interest and preferably wherein the entire target sequence and the PAM are within a non-coding region of the gene of interest. Distance of the targeted sequence (region of homology+PAM) from the excised region may not be critical, but in order to minimize the destabilization of the gene structure, the targeted sequence may be selected to be within less than 500, 400, 300, 200, 100, 90, 80, 70, 60, 50, 40, 30, 20 or less than 10 nucleotide from the considered end of the nucleotide repeat expansion. For example, considering the sgRNA which is designed to direct induction of a DSB 5' from the nucleotide repeat expansion, the most 3' nucleotide of the PAM of the targeted sequence is within less than 500, 400, 300, 200, 100, 90, 80, 70, 60, 50, 40, 30, 20 or less than 10 nucleotide from the most 5' nucleotide of the first (considering the 5' to 3' direction) nucleotide of the nucleotide repeat expansion to be excised. In addition, considering the sgRNA which is designed to direct induction of a DSB 3' from the nucleotide repeat expansion, the most 5' nucleotide of the region of homology of the targeted sequence is within less than 500, 400, 300, 200, 100, 90, 80, 70, 60, 50, 40, 30, 20 or less than 10 nucleotide from the most 3' nucleotide of the last (considering the 5' to 3' direction) nucleotide of the nucleotide repeat expansion to be excised. Preferably, in the practice of the present invention, when designing the sgRNA(s) disclosed herein, the skilled artisan will avoid excision of known regulatory elements present in the non-coding genomic DNA sequence around the nucleotide repeat expansion to be excised, such as regions for RNA processing/stability, such as polyA, splicing regions in introns, etc.

In a particular embodiment, the sgRNA molecules are designed for excising a trinucleotide repeat expansion located within the 3'-untranslated region of the DMPK gene. In a particular variant of this embodiment, the invention relates to a sgRNA molecule comprising a guide sequence selected in the group consisting of GCGCUCCCUGAACC-CUAGAACUGU (SEQ ID NO:1), ACGGGG-CUCGAAGGGUCCUUGUAG (SEQ ID NO:2), UGGG-GAGCGUCUGGCGCGAUCUCU (SEQ ID NO:3) and GUCGGGGUCUCAGUGCAUCCAAAA (SEQ ID NO:4).

The invention further relates to a vector as defined above, comprising a sequence coding a sgRNA molecule comprising a guide sequence selected from the group consisting of SEQ ID NO:1 to 4.

In another particular embodiment, the pair of sgRNA molecules is a pair of a sgRNA comprising a guide sequence selected from SEQ ID NO:1 and SEQ ID NO:2 and of a sgRNA comprising a guide sequence selected from SEQ ID NO:3 and SEQ ID NO:4.

In a further particular embodiment, the sgRNA used for inducing DSB upstream (or 5') of the trinucleotide repeat region is selected in the group consisting of:

(also referred to as sgRNA 1 in the experimental part, DNA binding sequence - i.e. the guide sequence - underlined):
SEQ ID NO: 5
GCGCUCCCUGAACCCUAGAACUGUGUUGUAGCUCCCUUUCGAAAGAACCG

UUGCUACAAUAAGGCCGUCUGAAAAGAUGUGCCGCAACGCUCUGCCCCUU

AAAGCUUCUGCUUUAAGGGGCAUCGUUUAUUUUUUUU (also referred to as sgRNA 7 in the experimental part, DNA binding sequence underlined)
SEQ ID NO: 6
GACGGGGCUCGAAGGGUCCUUGUAGGUUGUAGCUCCCUUUCGAAAGAACC

GUUGCUACAAUAAGGCCGUCUGAAAAGAUGUGCCGCAACGCUCUGCCCCU

UAAAGCUUCUGCUUUAAGGGGCAUCGUUUAUUUUUUUU

In a further particular embodiment, the sgRNA used for inducing DSB downstream (or 3') of the trinucleotide repeat region is selected in the group consisting of:

(also referred to as sgRNA E in the experimental part, DNA binding sequence underlined)
SEQ ID NO: 7
<u>GUGGGGAGCGUCUGGCGCGAUCUCUG</u>UUGUAGCUCCCUUUCGAAAGAACC

GUUGCUACAAUAAGGCCGUCUGAAAAGAUGUGCCGCAACGCUCUGCCCCU

UAAAGCUUCUGCUUUAAGGGGCAUCGUUUAUUUUUUUU (also referred to as sgRNA N in the experimental part, DNA binding sequence underlined)
SEQ ID NO: 8
<u>GUCGGGGUCUCAGUGCAUCCAAAA</u>GUUGUAGCUCCCUUUCGAAAGAACCG

UUGCUACAAUAAGGCCGUCUGAAAAGAUGUGCCGCAACGCUCUGCCCCUU

AAAGCUUCUGCUUUAAGGGGCAUCGUUUAUUUUUUUU

The invention further relates to a vector as defined above, comprising a sequence coding a sgRNA molecule having a sequence selected from the group consisting of SEQ ID NO:5 to 8.

In another embodiment, the pair of sgRNA molecules of the invention is a pair selected in the group consisting of SEQ ID NO:5 and SEQ ID NO:7; SEQ ID NO:5 and SEQ ID NO:8; SEQ ID NO:6 and SEQ ID NO:7; and SEQ ID NO:6 and SEQ ID NO:8. In a preferred embodiment, the pair of sgRNA molecules is selected in the group consisting of SEQ ID NO:5 and SEQ ID NO:8; SEQ ID NO:6 and SEQ ID NO:7; and SEQ ID NO:6 and SEQ ID NO:8.

As mentioned above, the sgRNA of the invention may be expressed from an expression cassette. Expression of the sgRNA may in particular be controlled by a promoter such as a U6 promoter. Accordingly, the invention also includes a cassette for expression of a sgRNA, comprising a sgRNA coding sequence placed under the control of a promoter such as the U6 promoter shown in SEQ ID NO:9.

In a particular embodiment, the expression cassette comprises the following sequence for expression of the sgRNA shown in SEQ ID NO:5 from a U6 promoter:

(SEQ ID NO: 10)
AGGTCGGGCAGGAAGAGGGCCTATTTCCCATGATTCCTTCATATTTGCAT

ATACGATACAAGGCTGTTAGAGAGATAATTAGAATTAATTTGACTGTAAA

CACAAAGATATTAGTACAAAATACGTGACGTAGAAAGTAATAATTTCTTG

GGTAGTTTGCAGTTTTAAAATTATGTTTTAAAATGGACTATCATATGCTT

ACCGTAACTTGAAAGTATTTCGATTTCTTGGCTTTATATATCTTGTGGAA

AGGACGAAACACCGCGCTCCCTGAACCCTAGAACTGTGTTGTAGCTCCCT

TTCGAAAGAACCGTTGCTACAATAAGGCCGTCTGAAAAGATGTGCCGCAA

CGCTCTGCCCCTTAAAGCTTCTGCTTTAAGGGGCATCGTTTATTTTTTTT

AA

In a particular embodiment, the expression cassette comprises the following sequence for expression of the sgRNA shown in SEQ ID NO:6 from a U6 promoter:

(SEQ ID NO: 11)
AGGTCGGGCAGGAAGAGGGCCTATTTCCCATGATTCCTTCATATTTGCAT

ATACGATACAAGGCTGTTAGAGAGATAATTAGAATTAATTTGACTGTAAA

CACAAAGATATTAGTACAAAATACGTGACGTAGAAAGTAATAATTTCTTG

GGTAGTTTGCAGTTTTAAAATTATGTTTTAAAATGGACTATCATATGCTT

ACCGTAACTTGAAAGTATTTCGATTTCTTGGCTTTATATATCTTGTGGAA

AGGACGAAACACCGACGGGGCTCGAAGGGTCCTTGTAGGTTGTAGCTCCC

TTTCGAAAGAACCGTTGCTACAATAAGGCCGTCTGAAAAGATGTGCCGCA

ACGCTCTGCCCCTTAAAGCTTCTGCTTTAAGGGGCATCGTTTATTTTTTT

TAA

In a particular embodiment, the expression cassette comprises the following sequence for expression of the sgRNA shown in SEQ ID NO:7 from a U6 promoter:

(SEQ ID NO: 12)
AGGTCGGGCAGGAAGAGGGCCTATTTCCCATGATTCCTTCATATTTGCAT

ATACGATACAAGGCTGTTAGAGAGATAATTAGAATTAATTTGACTGTAAA

CACAAAGATATTAGTACAAAATACGTGACGTAGAAAGTAATAATTTCTTG

GGTAGTTTGCAGTTTTAAAATTATGTTTTAAAATGGACTATCATATGCTT

ACCGTAACTTGAAAGTATTTCGATTTCTTGGCTTTATATATCTTGTGGAA

AGGACGAAACACCGTGGGGAGCGTCTGGCGCGATCTCTGTTGTAGCTCCC

TTTCGAAAGAACCGTTGCTACAATAAGGCCGTCTGAAAAGATGTGCCGCA

ACGCTCTGCCCCTTAAAGCTTCTGCTTTAAGGGGCATCGTTTATTTTTTT

TAA.

In a particular embodiment, the expression cassette comprises the following sequence for expression of the sgRNA shown in SEQ ID NO:8 from a U6 promoter:

(SEQ ID NO: 13)
AGGTCGGGCAGGAAGAGGGCCTATTTCCCATGATTCCTTCATATTTGCAT

ATACGATACAAGGCTGTTAGAGAGATAATTAGAATTAATTTGACTGTAAA

CACAAAGATATTAGTACAAAATACGTGACGTAGAAAGTAATAATTTCTTG

GGTAGTTTGCAGTTTTAAAATTATGTTTTAAAATGGACTATCATATGCTT

ACCGTAACTTGAAAGTATTTCGATTTCTTGGCTTTATATATCTTGTGGAA

AGGACGAAACACCGTCGGGGTCTCAGTGCATCCAAAAGTTGTAGCTCCCT

TTCGAAAGAACCGTTGCTACAATAAGGCCGTCTGAAAAGATGTGCCGCAA

CGCTCTGCCCCTTAAAGCTTCTGCTTTAAGGGGCATCGTTTATTTTTTTT

AA.

In SEQ ID NO:11 and 12 as represented above, the underlined G base was introduced because a G is required to start the transcription from the U6 promoter. However, those skilled in the art will understand that other promoters may not require a G in this position immediately preceding the guide coding sequence, or may require one or more other nucleotide bases as is well known in the art.

Methods and Uses of the Invention

The present invention contemplates various ways of reaching a target genomic DNA sequence with a Cas9 endonuclease and sgRNA molecules. In some embodiments, the Cas9 endonuclease is introduced within a cell in a polypeptide form. In a variant, the Cas9 endonuclease is conjugated to or fused to a cell penetrating peptide, which is a peptide that facilitates the uptake of a molecule into a cell. The sgRNA molecules may also be administered to the cell as isolated oligonucleotide, either directly or using transfection reagents such as lipidic derivatives, liposomes, calcium phosphate, nanoparticles, microinjection or electroporation.

In another embodiment, the present invention contemplates introducing the Cas9 endonuclease and/or sgRNA molecules into the target cell in the form of a vector expressing said endonuclease and/or sgRNA molecules. Methods of introducing and expressing genes into a cell are known in the art. The expression vector can be transferred into a host cell by physical, chemical, or biological means. The expression vector may be introduced in the cell using known physical methods such as calcium phosphate precipitation, lipofection, particle bombardment, microinjection, electroporation. Chemical means for introducing a polynucleotide into a host cell include colloidal dispersion systems, such as macromolecule complexes, nanocapsules, microspheres, beads, and lipid derivatives and liposomes. In other embodiments, the Cas9 endonuclease and/or the sgRNA molecules are introducing by biological means, in particular by a viral vector. Representative viral vectors useful in the practice of the invention include, without limitation, a vector derived from adenovirus, retrovirus, in particular lentivirus, poxviruses, herpes simplex virus I and adeno-associated virus (AAV). Selection of the appropriate viral vector will of course depend on the targeted cell and the virus tropism.

In an embodiment, the Cas9 endonuclease and the sgRNA molecules are provided within different vectors (such as two vectors, one containing a gene coding the Cas9 endonuclease, and a second coding both sgRNA molecules; or three vectors, one coding the Cas9 endonuclease and one vector for each sgRNA molecule). In another embodiment, all the elements of the CRISPR-Cas9 system, including the Cas9 endonuclease and both sgRNA molecules required for excision of the trinucleotide reapeat expansion, are expressed from a single expression vector.

The system of the present invention is used for excising a nucleotide repeat expansion within a non-coding region of a gene of interest. In an embodiment, the repeated nucleotide motif is a bi-, tri-, tetra-, penta- or hexanucleotide repeated, such as a CAG, CTG, CGG, GAA, AGG, CCG, CCTG, ATTCT, TGGAA, GGCCTG or GGGGCC repeat. In a particular embodiment, the repeat is within a gene of interest selected from FMR1, AFF2 or FMR2, AFF3, FXN, ATXN80S/ATXN8, ATXN10, PPP2R2B, BEAN1/TK2, NOP56, C9ORF72, ZN9/CNBP or DMPK. In a particular embodiment, the nucleotide repeat expansion is a trinucleotide repeat, such as a CAG, CTG, CGG, GAA, AGG or CCG repeat. In a further particular embodiment, the nucleotide repeat, in particular the trinucleotide repeat, is present within the 3' untranslated region of the DMPK gene. In a particular embodiment, the nucleotide repeat expansion (e.g. a trinucleotide repeat expansion) comprises from 20 to 10000 repeats of the nucleotide motif, more particularly from 50 to 5000 repeats. For example, the nucleotide repeat expansion to be excised (e.g. a trinucleotide repeat expansion) may comprise any number of repeats, such as at least 20, 30, 40, 50, 60, 70, 80, 90, 100, 200, 300, 400, 500, 600, 700, 800, 900, 1000 or at least more than 2000 repeats of the nucleotide motif. More specifically, the number of repeats is a pathological number of repeats, which means that said nucleotide repeat (e.g. a trinucleotide repeat) is associated, or may be associated, to a disease state. In a particular embodiment, the repeat is a CTG repeat within the 3'-untranslated region of the DMPK gene and is pathological from 50 or more repeats.

As used herein, the term "treating" and "treatment" refers to administering to a subject an effective amount of a composition so that the subject has a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Alternatively, treatment is "effective" if the progression of a disease is reduced or halted. "Treatment" can also mean prolonging survival as compared to expected survival if not receiving treatment. Those in need of treatment include those already diagnosed with a disorder associated with expression of a polynucleotide sequence, as well as those likely to develop such a disorder due to genetic susceptibility or other factors. As used herein, the term "treating" and "treatment" also refers the prevention of a disease or disorder, which means delaying or preventing the onset of such disease or disorder.

As used herein, a "nucleotide repeat expansion disorder" is a disease or disorder which is caused by or linked to a nucleotide repeat expansion where nucleotide repeats in certain genes exceed the normal, stable threshold, which differs per gene. nucleotide repeat expansion disorders include fragile X syndrome (FXS) and fragile X tremor ataxia syndrome (FXTAS), spinocerebellar ataxia type 8, 10, 12, 31 and 36, myotonic dystrophy type 1 and type 2, Friedreich's ataxia, Huntington-like 2 (HDL-2) disease and amyotrophic lateral sclerosis (C9-ALS).

In a particular embodiment, the methods of the present invention relate to the treatment of a nucleotide repeat expansion disorder wherein the nucleotide repeat expansion associated to the disorder is located within a non-coding region of a gene. These include for examples nucleotide repeat expansions located within an intron, a 5'-untranslated region or a 3'-untranslated region of a protein-coding gene.

In a particular embodiment, the nucleotide repeat expansion disorder is myotonic dystrophy, associated with a trinucletoide (such as a CTG) repeat expansion within the 3'-untranslated region of the DMPK gene.

In a particular embodiment, the nucleotide repeat expansion within the DMPK gene is excised using an appropriate pair of sgRNA molecules and an appropriate, matching to the selected sgRNAs, Cas9 endonuclease.

The sgRNA molecule, the pair of sgRNA molecules, the vector (either coding one or more sgRNA molecule and/or a Cas9 endonuclease) and the cell according to the invention can be formulated and administered to treat a variety of nucleotide repeat expansion disease states by any means that produces contact of the sgRNA molecule, the pair of sgRNA molecules, the vector and the cell with its site of action in the subject in need thereof.

The present invention also provides pharmaceutical compositions comprising a sgRNA or sgRNA pair of the invention, or the vector of the invention (coding either a sgRNA of the invention, or a pair of sgRNAs alone or together with a Cas9 endonuclease coding sequence), or the cell of the invention. Such compositions comprise a therapeutically effective amount of the therapeutic (the sgRNA(s), vector or cell of the invention), and a pharmaceutically acceptable carrier. In a specific embodiment, the term "pharmaceutically acceptable" means approved by a regulatory agency of the Federal or a state government or listed in the U.S. or European Pharmacopeia or other generally recognized pharmacopeia for use in animals, and humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents. These compositions can take the form of solutions, suspensions, emulsions, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the subject.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to, ease pain at the, site of the injection.

The amount of the therapeutic of the invention which will be effective in the treatment of a nucleotide repeat expansion can be determined by standard clinical techniques. In addition, in vivo and/or in vitro assays may optionally be employed to help predict optimal dosage ranges. The precise dose to be employed in the formulation will also depend on the route of administration, and the seriousness of the disease, and should be decided according to the judgment of the practitioner and each patient's circumstances. The dosage of the sgRNA(s), the vector or the cell administered to the subject in need thereof will vary based on several factors including, without limitation, the route of administration, the specific disease treated, the subject's age or the level of expression necessary to obtain the required the therapeutic effect. One skilled in the art can readily determined, based on its knowledge in this field, the dosage range required based on these factors and others.

Non-Limiting Objects of the Invention

The present application provides the following non-limiting objects:

1. A pair of sgRNA molecules, wherein said pair comprises a first and a second sgRNA molecules that able to bind by base-pairing a sequence complement to a target genomic DNA sequence which is located 5' and 3' from a nucleotide repeat expansion located within a non-coding region of a gene of interest, respectively, thereby being appropriate for excising said nucleotide expansion with a CRISPR/Cas9 system.

2. A sgRNA which comprises a sequence which is able to bind by base-pairing the sequence complement to a target genomic DNA sequence which is located 5' or 3' from a nucleotide repeat expansion within a non-coding region of a gene of interest.

3. The pair of sgRNA molecules according to object 1, or the sgRNA according to object 2, wherein said nucleotide repeat is located within an intron or within the 5'- or 3'-untranslated region (5'UTR or 3'UTR) of said gene of interest.

4. The pair of sgRNA molecules or the sgRNA according to object 3, wherein the nucleotide repeat is located within the 3'-UTR of said gene of interest.

5. A vector encoding the sgRNA or a pair of sgRNA molecules according to any one of objects 1 to 4, the vector being preferably a plasmid or a viral vector, such as a rAAV vector.

6. A target cell, which is transfected or transduced with the vector according to object 5.

7. A method for the production of a sgRNA or sgRNA pair, comprising culturing the target cell according to object 6 in conditions allowing production of said sgRNA or sgRNA pair, and recovering said sgRNA or said pair of sgRNA molecules from said culturing step.

8. An in vitro method for excising a nucleotide repeat located within a non-coding region of a gene in a cell, comprising introducing in said cell a pair of sgRNA molecules according to any one of objects 1 and 3 to 4, or a vector according to object 5, and a CRISPR/Cas9 endonuclease.

9. The method according to object 8, wherein the Cas9 endonuclease is derived from *S. pyogenes, S. thermophilus, S. aureus, N. meningitidis, S. mutans, C. jejuni, F. novicida, P. multocida, P. bettyae, H. parainfluenzae, H. pittmaniae* or *L. crispatus*, preferably from *N. meningitidis*.

10. A sgRNA pair according to any one of object 1 and 3 to 4, or a vector according to object 5, for use in combination with a Cas9 endonuclease in a method for treating a nucleotide repeat expansion disorder, wherein the sgRNA molecules of the sgRNA pair are designed to excise a nucleotide repeat expansion associated to said disorder from a non-coding region of a gene of interest.

11. The sgRNA pair for use according to object 10, wherein the nucleotide repeat expansion is a bi-, tri-, tetra-, penta or hexanucleotide repeat expansion, in particular a trinucleotide repeat expansion.

12. The sgRNA pair for use according to object 10 or 11, wherein the nucleotide repeat expansion is located within the 3'-UTR of said gene of interest.

13. The sgRNA pair for use according to any one of objects 10 to 12, wherein said disorder is fragile X syndrome and fragile X tremor ataxia syndrome, spinocerebellar ataxia type 8, 10, 12, 31 and 36, myotonic dystrophy type 1 and 2, Friedreich's ataxia, Huntington-like 2 disease and amyotrophic lateral sclerosis type C9-ALS.

14. The sgRNA according to object 2 to 4, or the sgRNA pair for use according to any one of objects 10 to 13, wherein the gene of interest is FMR1, AFF2 or FMR2, AFF3, FXN, ATXN80S/ATXN8, ATXN10, PPP2R2B, BEAN1/TK2, NOP56, C9ORF72, ZN9/CNBP or DMPK.

15. The sgRNA pair for use according to any one of objects 10 to 14, wherein the disorder is myotonic dystrophy type 1 and the gene of interest is the DMPK gene.

EXAMPLES

Materials and Methods
Construction of Plasmids

List of the plasmids used and constructed in this study is given in TABLE 3. Cloning experiments have been carried out in chemical competent *Escherichia coli* DH10B (Invitrogen). Expression cassettes for the protein Cas9 from *Neisseria meningitides* (NM) are listed as pC512-Int-NMCas9-smSVpolyA and pEFS-Int-NMCas9-SVpolyA. Both of them contain the human optimized sequence of NMCas9 under the control of either the synthetic muscle-specific promoter C5-12 or the ubiquitous EFS promoter (shorter version of the EF-1α promoter). NMCas9 sequence contains also two nuclear localization signal (NLS), one per terminus, the human influenza hemagglutinin epitope (HA) and three tandem FLAG epitopes (3XFLAG) at the C-terminus. The sequence of NM Cas9 was PCR amplified from plasmid JDS246NMCas9 (provided by Jean Paul Concordet) and cloned into the AAV plasmids pC512-Int-smSVpolyA and pEFS-Int-SVpolyA, each one containing the indicated promoter, a chimeric intron and a SV40 polyadenylation signal (sm: shorter version).

Expression cassette for the NM single guide RNA (sgRNA), pBlue_Double_U6sgRNAs_NM, was designed in order to contain twice in tandem the human optimized sequence for the scaffold (constant part) of the NM sgRNA under the control of the U6 promoter. The construct holds two different restriction cloning sites where to introduce the string of the sgRNA specific for the genomic target (protospacer), BbsI and BspMI. The sequence of the sgRNA scaffold was provided by Jean Paul Concordet and modified at the protospacer cloning sites. Double_U6sgRNAs_NM construct was synthetically synthesized and cloned into plasmid pBluescript SK(+) by GeneCust.

sgRNA protospacers 1, 7, E and N have been designed as described in section "Design of the sgRNAs" (see below). As first sgRNAs 1 and 7 have been cloned into BbsI site of plasmid pBlue_Double_U6sgRNAs_NM to originate plasmids pBlue-U6gRNA-NM-1-DMPK and pBlue-U6gRNA-NM-7-DMPK. sgRNAs E and N have been cloned into BsbMI site of the latter to originate the the following combinations: pBlue-U6gRNA-NM-1N-DMPK, pBlue-U6gRNA-NM-7E-DMPK and pBlue-U6gRNA-NM-7N-DMPK. In order to select by sorting cells transfected with the sgRNAs the constructs described above were enzymatically digested by SnaBI and cloned into a plasmid containing a nuclear GFP, pAAV-Des-AcGFP.

Design of the sgRNAs

The genomic region of the DMPK 3'UTR surrounding the CTG repeats was manually screened for the presence of protospacer adjacent motifs (PAMs) specific for *Neisseria meningitidis* (NM). Beside the consensus sequence of NM PAM GATT) [Zhang Y et al Mol Cell 2013], the following variants, tested by Esvelt and colleagues in *Escherichia coli* [Esvelt K M et al Nature Methods 2013], have also been taken into account: NNNNGNTT, NNNNGANT, NNNNGTTN. Considering both, the position of the targets and PAMs within the 3'UTR region and also the number of potential off-targets (calculated by CasOFFinder setting the number of mismatches cutoff ≤6) four sgRNAs were selected, two targeting the region upstream the CTG repeat (sgRNA 1 and 7) and the other two targeting the region downstream the CTG repeat (sgRNA E and N). Only one of them is relative to a consensus PAM (sgRNA N), indeed the others are relative, two to the variant NNNNGANT (sgRNA 1 and 7), and one to the variant NNNNGNTT (sgRNA E) (FIG. 3). sgRNAs were designed in order to target a genomic sequence that is 24 nt and in order be cloned into BsbI site (sgRNA 1 and 7) or BspMI site (sgRNA E and N) of plasmid pBlue_Double_U6sgRNAs_NM. Moreover the nucleotide G was added to the 5' of sgRNA 7 and E (already present in the 5' of the other sgRNA) to optimize U6-driven transcription. All sgRNAs were synthetically synthesized as simple forward and reverse primers (see primers list) and then annealed in vitro prior the ligation with pBlue_Double_U6sgRNAs_NM plasmid (or derivatives) digested with the appropriate restriction enzymes.

Cell Culture and Transfection Assay to Test Nuclease Activity

Cells were seeded 1 day before transfection, harvested 2 days post transfection and kept at −80° C. until genomic DNA extraction unless stated otherwise. Standard temperature of 37° C. and 5% $CO_2$ were used to grow and maintain the cells in culture. Details for the transfection assays are described below.

HeLa cells and HEK 293T cells were cultured in Dulbecco's modified Eagle medium (DMEM) with high glucose and GlutaMAX (Invitrogen), supplemented with 10% Fetal Bovin Serum (FBS, Invitrogen). Cells were seeded in 12 wells plate, 0.5-1.0×$10^5$/well for HeLa cells, 0.25×$10^5$ cells/well for HEK 293T, in a final volume=1 ml (~80% confluency the day of transfection). Transfection reactions were prepared as follow: 3 µl of FuGENE HD transfection reagent and 1 µg of total DNA (FuGENE-DNA ratio 3:1) in 50 µl of medium without serum. NMCas9 and sgRNAs ratio was 3:1.

Primary human fetal myoblast were grown in skeletal muscle cell growth medium (PromoCell) supplemented with 15% FBS. In order to reach ~50% of confluency the day of transfection ~0.3-0.5×$10^5$ cells were seeded/10 cm petri dish (final volume=8 ml). Cells were transfected with JetPEI transfection reagent (Polyplus transfection) in a ratio 2:1 with the DNA and in a final volume of 500 µl of 150 mM NaCl (12 µl transfection reagent for 6 µg of total DNA; NMCas9-sgRNAs ratio 1:1). Transfection reactions were incubated for 30 min at RT and growth medium was changed before their addition.

PCR Assay to Test the Genomic Deletion

Genomic DNA from HeLa cells and HEK 293T cells was extracted using GeneJET Genomic DNA Purification Kit (Thermo Scientific) and eluted in a final volume of 150 µl.

Genomic DNA from sorted and unsorted primary human fetal myoblast was extracted using QIAamp DNA Micro and Mini Kit (QIAGEN) and eluted in a final volume of 30 and 200 µl respectively.

PCR was performed using Platinum Taq DNA Polymerase High Fidelity (Invitrogen), 10% DMSO, 100-150 ng total gDNA and primers F1- and R1-DMPK-3'UTR. PCR products were separated by electrophoresis: 15-20 µl of each PCR reaction were loaded into a 1.5% agarose gel containing GelRed DNA stain (electrophoresis run done at 90-100 Volt for 1 h 15-30 min). After electrophoresis gels' images were taken upon exposition at the UV and adjusted for brightness and contrast.

Sequencing of the PCR products containing the deletion of the CTG repeat was done subcloning in order to sequence single clones. PCR was performed as described above with primers F1-DMPK-3UTR-KpnI and R1-DMPK-3UTR-XbaI. PCR products were separated by electrophoresis in a 2% low melting temperature agarose gel and DNA bands relative to PCR products containing the deletion of the CTG repeats were gel extracted, digested with KpnI and XbaI and cloned into plasmid pBluescript II SK(+) digested with the same restriction enzymes. Plasmids were extracted from positive clones and sent for sequencing with primer pBlue_MCS_before2.

Western Blotting

Cells were lysed on ice in 100 µl lysis buffer containing 150 mM NaCl, 10 mM Tris-HCl (pH 7.4), 1 mM EGTA, 1 mM EDTA, 100 mM sodium fluoride, 4 mM sodium pyrophosphate, 2 mM sodium orthovanadate, 1% Triton X-100 and 0.5% IGEPAL supplemented with a complete protease inhibitor cocktail (Roche). Concentrations of the total protein extract were determined by Bio-Rad Protein Assay Kit (Bio-Rad). Proteins were separated by electrophoresis SDS-PAGE on 10% precast gel (Bio-Rad) and, then transferred to nitrocellulose membrane. In order to prevent unspecific binding, membranes were soaked in a blocking solution (50% odyssey solution 50% TBST solution [0.1% Tween in 1M Tris-HCl pH 7.6]) for 2 hours prior overnight incubation with antibodies directed against Flag epitope (monoclonal anti-Flag M2, 1:3'000; Sigma). The day after excess of the antibodies was washed in TBST and membrane were incubated with a secondary antibody alexa-conjugated (Goat Anti-Mouse Alexa Fluor 680, 1:10'000; Invitrogen) for 1 hour. Protein bands were visualized by infrared fluorescence using Odyssey Imaging System (LICOR Biotechnology, Inc.).

Results

Cas9 and sgRNA Expression Constructs

Among all available CRISPR/Cas9 systems, we selected that one originating from the bacterium *Neisseria meningitidis* (NM) because NMCas9 is of small size and can fit into an adeno-associated virus (AAV) vector. In addition, we found by manual screening the presence of potential target sites for NMCas9 within the 3' untranslated region (3'-UTR) of the human DMPK gene. We generated two AAV constructs that contain the human optimized NMCas9 coding sequence (3.25 Kb) under either the ubiquitous EFS (shorter version of the Elongation Factor 1 alpha) promoter or the muscle-specific C5-12 promoter. We also included other regulatory sequences in the constructs, a chimeric intron located downstream each promoter to stabilize Cas9 mRNA, and a simian virus 40 polyadenylation signal (SV40 polyA). Cas9 was fused to two nuclear localization signals (NLS), one at each terminus, in order to address the protein into the nucleus, and HA (derived from human influenza hemagglutinin) and Flag epitopes, which are useful for protein detection. The scheme of the constructs is represented in FIGS. 1, A and B.

We tested the functionality of Cas9 expression cassettes in vitro in cell lines (FIG. 2) and in vivo in wild type C57Bl/6 mice (data not shown). Briefly, cells were transfected with Cas9 constructs and, two days post-transfection, they were either lysed for total protein extraction or fixed for labeling experiments. NMCas9 was detected in HeLa and C2C12 cells at the expected molecular size by western blotting analysis (FIG. 2) and in the nucleus of cells by immunofluorescence (data not shown) with antibodies directed against the Flag epitope.

In order to delete the CTG repeat from the 3'UTR region of the human DMPK gene, we designed sgRNAs located upstream and downstream this CTG repeat region, which could drive NMCas9-mediated DNA double cut after the DMPK stop codon sequence and before the polyA signal. Thus, we designed an expression cassette containing two sgRNA scaffolds, each one under the control of the U6 promoter and located in tandem in the same plasmid (FIG. 1, construct C). Four sgRNA protospacers were selected minimizing off-target effects (see respective genomic targets in FIG. 3 & Table 1) and cloned into BbsI and BspmI cloning sites preceding the sgRNA scaffolds.

TABLE 1

Protospacer and protospacer adjacent motif (PAM) DNA sequences

| Target name | Target DNA sequence (protospacer) + PAM DNA sequence (underlined) | Position# (start-end) | Strand | SEQ ID NO |
|---|---|---|---|---|
| 1 | GCGCTCCCTGAACCCTAGAACTGT<u>CTTCGACT</u> | 46273725-46273756 | − | SEQ ID NO: 15 |
| 7 | ACGGGGCTCGAAGGGTCCTTGTAG<u>CCGGGAAT</u> | 46273524-46273555 | − | SEQ ID NO: 16 |
| E | TGGGGAGCGTCTGGCGCGATCTCT<u>GCCTGCTT</u> | 46273258-46273289 | − | SEQ ID NO: 17 |
| N | GTCGGGGTCTCAGTGCATCCAAAA<u>CGTGGATT</u> | 46273057-46273088 | + | SEQ ID NO: 18 |

Human genome reference: February 2009 (GRCh37/hg19)

We generated three different sgRNA couples that could potentially drive the deletion of the CTG repeat expansion (β, γ, and δ, Table 2).

TABLE 2 sgRNA couples and expected deletion size

| | | Cas9 + sgRNAs | | |
| sgRNA couple | No sgRNA | β (1 + N) | γ (7 + E) | δ (7 + N) |
|---|---|---|---|---|
| Total number of potential off-targets⁺ | | 9 + 8 = 17 | 6 + 6 = 12 | 6 + 8 = 14 |
| Size of the excised DNA fragment | | 658# | 266# | 457# |
| PCR product expected size (bp)⁺⁺⁺ | 891* | 233# | 625# | 434# |

⁺Considering a number of mismatches ≤6, checked by Cas-OFFinder
⁺⁺⁺With primers F1-DMPK-3UTR and R1-DMPK-3UTR
*Size calculated for a number of CTG repeat (n CTG) = 20 (861* for HeLa cells [n CTG = 10]; 846* for 293T cells [n CTG = 5])
size calculated considering a precise cut between the 3$^{rd}$ and the 4$^{th}$ nucleotide upstream the PAM sequence These constructs were also subcloned into an AAV plasmid harboring the sequence for a green fluorescent protein (FIG. 1, construct D & material and methods).

Cas9-Mediated Deletion of the CTG Repeat Expansion in the Human DMPK Gene

In order to test if the designed sgRNAs were able to address NMCas9 to the corresponding genomic DNA target regions, we co-transfected HeLa cells (or HEK 293T) cells with the plasmid that contains the EFS-NMCas9 expression cassette and each one of the three plasmids harboring a couple of sgRNA, and appropriate controls (table 2 and FIG. 4). DNA was then extracted from the cells and used as template in a PCR reaction to amplify a region of 891 bp in length that includes all the genomic DNA targets (F1- and R1-DMPK-3'UTR primers, FIG. 3). Agarose gel of the PCR products is shown in FIG. 4. sgRNAs couples (β, γ and δ) resulted in the PCR-amplification of the 891 bp DNA fragment and a smaller fragment corresponding to expected DNA region after CRISPR/Cas9-mediated excision (FIG. 4, red arrow). These smaller size PCR products were subcloned and sequenced to verify their identity. Results from sequencing the PCR products obtained with the sgRNA couples β (1 plus N) and δ (7 plus N) are represented in FIG. 6 and demonstrated that, in the majority of the clones, NMCas9 cutting sites were located at either nucleotide $N_3$ or $N_4$ of the target sequence adjacent to the PAM (#n). Therefore, these results demonstrate the efficacy of the designed sgRNAs in driving NMCas9-mediated deletion of the genomic DNA flanking the DMPK CTG repeat.

We also tested the efficacy of this CRISPR/Cas9 system in the human DMPK locus in the presence of a pathological CTG expansion. For that purpose, primary cells derived from a DM1 patient carrying a 200 CTG repeat (DM200) were co-transfected with EFS-NMCas9 and sgRNA γ (sgRNAs 7 plus E, construct D) plasmids, and primary cells from a normal individual (Ctrl) were used as control (FIG. 1). Genomic DNA was extracted from GFP-positive sorted Ctrl and DM200 cells in order to increase the proportion of DNA originating from cells expressing the sgRNAs. A PCR was performed as described above and resulted in the amplification of small DNA fragments in Ctrl and DM200 cells that corresponded in size to fragments originating from the expected excised genomic DNA region (FIG. 5, red arrow).

We also observed PCR products of full and partial lengths corresponding to uncut genomic DNA (FIG. 5, green and blue arrows, respectively). The latter is likely a partial amplification of the entire genomic DNA region of the DM1 patient as 200 CTG repeats cannot be easily amplified by PCR.

Altogether, these results show that the described Cas9-sgRNA system is suitable for excising the CTG repeat from the 3'UTR region of the human DMPK gene.

The invention claimed is:

1. A pair of sgRNA molecules comprising:
    a first sgRNA comprising a guide sequence selected from SEQ ID NO:1 and SEQ ID NO:2; and
    a second sgRNA comprising a guide sequence selected from SEQ ID NO:3 and SEQ ID NO:4.

2. The pair of sgRNA molecules according to claim 1, wherein:
    the first sgRNA is selected from the group consisting of SEQ ID NO:5 and SEQ ID NO:6; and
    the second sgRNA is selected from the group consisting of SEQ ID NO:7 and SEQ ID NO:8.

3. An in vitro method for excising a nucleotide repeat located within a non-coding region of the DMPK gene in a cell comprising the DMPK gene, comprising introducing in said cell the pair of sgRNA molecules of claim 2 and the CRISPR/Cas9 endonuclease from *N. meningitidis*.

4. A vector encoding the pair of sgRNA molecules of claim 1.

5. The vector of claim 4, wherein the vector is a plasmid or a viral vector.

6. The vector of claim 5, wherein the vector is a rAAV vector.

7. An isolated target cell, which is transfected or transduced with the vector according to claim 4.

8. A method for the production of the pair of sgRNAs, comprising culturing the target cell according to claim 7 to produce said pair of sgRNAs, and recovering said pair of sgRNAs from the culture.

9. An in vitro method for excising a nucleotide repeat located within a non-coding region of the DMPK gene in a cell comprising the DMPK gene, comprising introducing in said cell the pair of sgRNA molecules of claim 1 and the CRISPR/Cas9 endonuclease from *N. meningitidis*.

10. A sgRNA comprising a guide sequence selected from the group consisting of SEQ ID NO:1, SEQ ID NO:2, SEQ ID NO:3, and SEQ ID NO:4.

11. The sgRNA according to claim 10, wherein said sgRNA is selected from the group consisting of SEQ ID NO:5, SEQ ID NO:6, SEQ ID NO:7, and SEQ ID NO:8.

12. A vector encoding the sgRNA of claim 10.

13. The vector of claim 12, wherein the vector is a plasmid or a viral vector.

14. The vector of claim 12, wherein the vector is a rAAV vector.

15. An isolated target cell, which is transfected or transduced with the vector according to claim 12.

16. A method for the production of the sgRNA, comprising culturing the target cell according to claim 15 to produce said sgRNA, and recovering said sgRNA from the culture.

* * * * *